United States Patent [19]

Murdock

[11] Patent Number: 4,900,838

[45] Date of Patent: Feb. 13, 1990

[54] ACYLATION PRODUCTS OF BIS(2-IMIDAZOLIN-2-YLHYDRAZONES) OF 9,10-ANTHRACENEDICARBOXALDEHYDE

[75] Inventor: Keith C. Murdock, Pearl River, N.Y.

[73] Assignee: American Cyanamid Company, Stamford, Conn.

[21] Appl. No.: 247,989

[22] Filed: Sep. 22, 1988

Related U.S. Application Data

[63] Continuation-in-part of Ser. No. 91,077, Aug. 31, 1987, abandoned, which is a continuation-in-part of Ser. No. 922,220, Oct. 23, 1986, abandoned.

[51] Int. Cl.$^4$ .................. C07D 233/46; C07D 233/44; C07F 9/65
[52] U.S. Cl. .................................... 548/111; 548/316; 548/350
[58] Field of Search ...................... 548/350, 316, 111; 514/94, 392, 402

[56] References Cited

U.S. PATENT DOCUMENTS 2,843,586 7/1958 Melamed ........................ 548/111 X
3,519,639 7/1970 Budde et al. ........................ 548/111

OTHER PUBLICATIONS

Kosolapoff, G., *Organophosphorous Compounds*, John Wiley, New York, 1950, p. 279.
*Chemical Abstracts*, 93: 204742y (1980), [Blackburn, G., et al., *J. Chem. Soc., Perkin Trans.* 1, 1980, (5), 1150–3].

*Primary Examiner*—Richard A. Schwartz
*Attorney, Agent, or Firm*—Alan M. Gordon

[57] ABSTRACT

N-acylated derivatives of bis(2-imidazolin-2-ylhydrazones) of 9,10-anthracenedicarboxaldehyde, useful as anti-cancer agents against certain strains in mice, are disclosed and described, including processes for manufacture and use.

39 Claims, No Drawings

ACYLATION PRODUCTS OF BIS(2-IMIDAZOLIN-2-YLHYDRAZONES) OF 9,10-ANTHRACENEDICARBOXALDEHYDE

This application is a continuation-in-part of Ser. No. 091,077, filed Aug. 31, 1987, now abandoned, which in turn is a continuation-in-part of Ser. No. 922,220, filed Oct. 23, 1986, now abandoned.

BRIEF SUMMARY OF THE INVENTION

This invention is concerned with new organic compounds which are N-acylated derivatives of bis(2-imidazaolin-2-ylhydrazones) of 9,10-anthracendicarboxaldehyde.

The unacylated precursor compounds are disclosed in U.S. Pat. No. 4,258,181, the contents and disclosure of which are hereby incorporated by reference.

Specifically this invention is concerned with compounds of the formula:

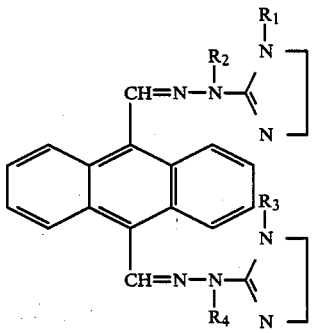

wherein $R_1$ and $R_3$ are the same or different and are: hydrogen, alkyl($C_1$-$C_6$),

((where $R_5$ is hydrogen, alkyl($C_1$-$C_6$), cyclohexyl which is further substituted by carboxyl, phenyl, monosubstituted phenyl (wherein the substituent may be ortho, meta or para and is fluoro, nitro, alkyl($C_1$-$C_6$), alkoxy($C_1$-$C_3$) or cyano), pentafluorophenyl, naphthyl, furanyl,

—$CH_2CH_2COOH$, —$OC(CH_3)_3$, —$CH_2OCH_3$, ($CH_2)_3COOH$,

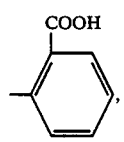

—$(CH_2)_2SO_3H$ or —$CH_2N^{\oplus}$—$(CH_3)_3Cl^{\ominus}$));

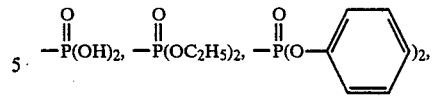

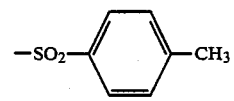

or —$SO_3H$; with the proviso that only one of $R_1$ and $R_3$ may be hydrogen or alkyl($C_1$-$C_6$); $R_2$ and $R_4$ are the same or different and are: hydrogen, alkyl($C_1$-$C_4$) or

((where $R_6$ is hydrogen, alkyl($C_1$-$C_6$), phenyl, monosubstituted phenyl (wherein the substituent may be in the ortho, meta or para position and is fluoro, nitro, alkyl($C_1$-$C_6$), alkoxy($C_1$-$C_3$) or cyano), pentafluorophenyl, naphthyl, furanyl or —$CH_2OCH_3$)); together with the pharmacologically acceptable salts thereof.

Special mention is made of the di- and monophosphoramidic acids embraced by the foregoing formula. Their anti-tumor activity is coupled with a lack of painful phlebitis near the site of injection when administered to some warm-blooded animals.

DETAILED DESCRIPTION OF THE INVENTION

The compounds of the present invention are obtainable as yellow to orange crystalline materials having characteristic melting points and absorption spectra, and which may be purified by recrystallization from common organic solvents such as lower alkanols, dimethylformamide, methyl isobutyl ketone and the like.

The compounds of the present invention may be readily prepared in accordance with the following reaction scheme:

Scheme

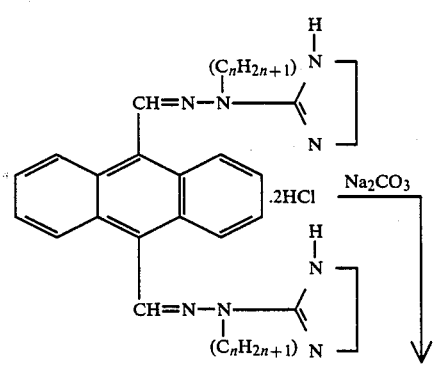

-continued
Scheme

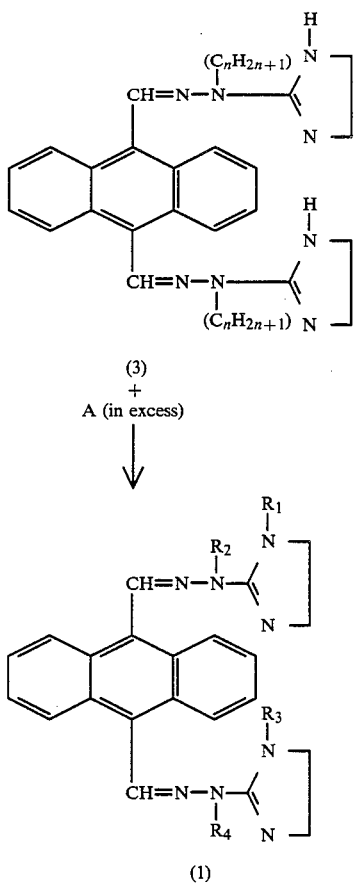

where A is an acylating agent including carboxylic acid anhydrides and acid chlorides, sulfonyl chlorides and the diester of a phosphoric acid chloride and where $R_1$, $R_2$, $R_3$ and $R_4$ are as hereinbefore defined.

An acylating anhydride may be employed without the need of an acid-binding agent. However, when acid chlorides are used in the acylation process, a non-basic acid-binding agent is employed to prevent major formation of bis(2-imidazolin-2-ylhydrazone) of 9,10-anthracenedicarboxaldehyde dihydrochloride as an undesired byproduct. A convenient non-basic acidbinding agent which is used for this purpose is N,O-bis(-trimethylsilyl) acetamide.

In accordance with the above reaction scheme, bis(2-imidazolin-2-ylhydrazone) of 9,10-anthracenedicarboxaldehyde dihydrochloride or an N,N'-dialkyl derivative (4), disclosed in U.S. Pat. No. 4,258,181, is treated with an aqueous solution of sodium carbonate and is allowed to stand for several hours to precipitate the free base compound (3). The product is collected by filtration, then dried in vacuo at about 110° C. for about 15 hours.

When the acylating agent A is an anhydride such as butyric anhydride, succinic anhydride, glutaric anhydride or 1,2-cyclohexane dicarboxylic anhydride and the like, the following procedure applies: The dried free base (3) is suspended and stirred in a dried solvent such as dichloromethane or N,N-dimethylformamide and the like, in an inert atmosphere, e.g., under nitrogen or argon and the like, then an excess of the anhydride (2) is added and stirring is continued until the solid is dissolved. The solution is allowed to stand at about 23° C. for 8–48 hours. The product (1) precipitates either spontaneously or after addition of ether or water, then is collected by filtration.

When the acylating agent (2) is an acid chloride such as benzoyl chloride, methoxyacetyl chloride, p-hexylbenzoyl chloride, m-nitrobenzoyl chloride, 2-furoyl chloride or diethyl chlorophosphate and the like, the following procedure is used: The dried bis(2-imidazolin-2-ylhydrazone) of 9,10-anthracenedicarboxaldeyde free base (3) is suspended and stirred in dichloromethane or the like, under argon or nitrogen in a closed round bottom flask equipped with a stirrer and a rubber septum cap, then an acid binding agent such as N,O-bis(-trimethylsilyl)acetamide is added with stirring, using a weighed hypodermic syringe to inject the reagent through the rubber septum. Then the desired acid chloride is added in the same manner. The reaction mixture is stirred from three to sixty-four hours. The solution or suspension is chromatographed by dry column chromatography on alumina, and eluted with solvents such as dichloromethane, ethyl acetate, chloroform, acetone and the like. The cuts are collected and evaluated by thin layer chromatography on silica gel using solvent systems such as 3/1, 19/1 or 39/1 of chloroform/methanol, then the cuts containing the desired products are evaporated and purified by conventional means.

When, for example, the alkyl esters of mono- and di-phosphonic acid derivatives are to be converted to the corresponding free phosphonic acids, in an elegant modification according to this invention, a triarylphosphine, preferably triphenylphosphine, will be used with the cleaving agent, e.g. iodotrialkylsilane, to remove byproduct alkyl iodide, thus precluding alkylation in other positions. This will be exemplified hereinafter.

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), by Deran, Greenberg, MacDonald, Schumacher and Abbott. These protocols have established standardized screening tests which are generally followed in the field of testing for antitumor agents. Three of these systems are particularly significant to the present invention. They are lymphocytic leukemia P388, melanotic melanoma B16 and lymphocytic leukemia L1210. All of these neoplasms grow in mice.

Lymphocytic leukemia P388 test

The animals used were BDF1 mice all of one sex per test, weighing a minimum of 17 g and all within a 3 g weight range per test. There were 6 animals per test group. The tumor transplant was by intraperitoneal injection of 0.5 ml of diluted ascitic fluid containing $10^6$ cells of lymphocytic leukemia P388. The test compounds were administered intraperitoneally on days 1, 5 and 9 (relative to tumor inoculation) at various doses. The animals were weighed and survivors recorded on a regular basis for 60 days. The median survival time and the ratios for treated (T)/control (C) animals were calculated. The positive control compound was either 5-fluorouracil, given as a 60 mg/kg injection, or bis(2-imidazolin-2-ylhydrazone) of 9,10-anthracenedicarboxaldehyde dihydrochloride hereinafter called positive control A or B, respectively, given as a 25 mg/kg injection. The results of this test with representative compounds of the present invention appear in Table I.

TABLE I

Lymphocytic Leukemia P388 Test

| Compound | Dose (mg/kg) | Median Survival (Days) | T/C × 100 % |
|---|---|---|---|
| 2-[[10-[[Acetyl(1-acetyl-4,5-dihydro-1H—imidazol-2-yl)hydrazono]methyl]-9-anthracenyl]methylene]-1-(4,5-dihydro-1H—imidazol-2-yl)hydrazide of acetic acid | 200 | 17.5 | 175 |
| | 100 | 17 | 170 |
| | 50 | 16.5 | 165 |
| | 25 | 15.5 | 155 |
| | 12.5 | 13 | 130 |
| | 6.25 | 12.5 | 125 |
| Control | — | 10 | — |
| Positive Control B | 25 | 21.5 | 215 |
| 2,2'-[9,10-Anthracenediylbis(methylidyne-1-hydrazinyl-2-ylidene)]bis[4,5-dihydro-1-(1-oxobutyl)-1H—imidazole | 200 | 15.5 | 155 |
| | 100 | 14.5 | 145 |
| | 50 | 14 | 140 |
| | 25 | 12.5 | 125 |
| | 12.5 | 12.5 | 125 |
| Control | — | 10 | — |
| Positive Control B | 25 | 21.5 | 215 |
| 2,2'-[9,10-Anthracenediylbis(methylidyne-1-hydrazinyl-2-ylidene)]bis[4,5-dihydro-gamma-oxo-1H—imidazole-1-butanoic acid] | 12.5 | 23 | 230 |
| | 6.25 | 19 | 190 |
| | 3.12 | 19 | 190 |
| | 1.56 | 17 | 170 |
| | 0.78 | 17 | 170 |
| | 0.39 | 15.5 | 155 |
| | 0.19 | 15 | 150 |
| Control | — | 10 | — |
| Positive Control A | 60 | 17.5 | 175 |
| [9,10-Anthracenediylbis[methylidyne-1-hydrazinyl-2-ylidene(4,5-dihydro-1H—imidazol-2,1-diyl)]]bisphosphonic acid, tetraphenyl ester | 200 | 16 | 160 |
| | 100 | 15.5 | 155 |
| | 50 | 13 | 130 |
| Control | — | 10 | — |
| Positive Control A | 60 | 17.5 | 175 |
| [9,10-Anthracenediylbis[methylidyne-1-hydrazinyl-2-ylidene(4,5-dihydro-1H—imidazole-2,1-diyl)]]bisphosphonic acid, tetraethyl ester | 100 | 12 | 120 |
| Control | — | 10 | — |
| Positive Control A | 60 | 17.5 | 175 |
| [9,10-Anthracenediylbis[methylidyne-1-hydrazinyl-2-ylidene(4,5-dihydro-1H—imidazole-2,1-diyl)]]biphosphonic acid | 25 | 36.5 | 365 |
| | 12.5 | 27.5 | 275 |
| | 6.25 | 22 | 220 |
| | 3.12 | 18 | 180 |
| | 1.56 | 17 | 170 |
| | 0.78 | 17.5 | 175 |
| Control | — | 10 | — |
| Positive Control A | 60 | 17.5 | 175 |
| 2,2'-(9,10-Anthracenediyldimethylidyne)bis[1-(1-benzoyl-4,5-dihydro-1H—imidazol-2-yl)hydrazide] of benzoic acid | 200 | 32 | 320 |
| | 100 | 23 | 230 |
| | 50 | 20 | 200 |
| | 25 | 19.5 | 195 |
| | 12.5 | 19 | 190 |
| | 6.25 | 18 | 180 |
| | 3.12 | 17 | 170 |
| | 1.56 | 17.5 | 175 |
| | 0.78 | 15.5 | 155 |
| Control | — | 10 | — |
| Positive Control A | 60 | 23 | 230 |
| 2,2'-9,10-Anthracenediyldimethylidyne)bis[1-[4,5-dihydro-1-(methoxyacetyl)-1H—imidazol-2-yl]hydrazide] of methoxyacetic acid | 200 | 16.5 | 150 |
| | 50 | 16.5 | 150 |
| | 12.5 | 16.5 | 150 |
| | 3.12 | 14.5 | 132 |
| Control | — | 11 | — |
| Positive Control B | 25 | 32.5 | 295 |
| 2,2'-[9,10-Anthracenediylbis(methylidyne-1-hydrazinyl-2-ylidene)]bis[4,5-dihydro-delta-oxo-1H—imidazole-1-pentanoic acid] | 200 | 23 | 209 |
| | 50 | 19 | 173 |
| | 12.5 | 18 | 164 |
| | 3.12 | 15.5 | 141 |
| Control | — | 11 | — |
| Positive Control B | 25 | 32.5 | 295 |
| 2,2'-[9,10-Anthracenediylbis(methylidyne-1-hydrazinyl-2-ylidene)]bis[4,5-dihydro-1-[(4-methylphenyl)sulfonyl]-1H—imidazole] | 200 | 14 | 127 |
| | 50 | 14 | 127 |
| Control | — | 11 | — |
| Positive Control B | 25 | 32.5 | 295 |
| 2,2'-(9,10-Anthracenediyldimethylidyne)bis[1-[1-(4-hexylbenzoyl)-4,5-dihydro-1H—imidazol-2-yl]hydrazide] of 4-hexylbenzoic acid | 200 | 14 | 127 |
| Control | — | 11 | — |
| Positive Control A | 60 | 20 | 182 |
| 2,2'-(Anthracenediyldimethylidyne)bis[1-[4,5-dihydro-1-(3-nitrobenzoyl)-1H—imidazol-2-yl]hydrazide] of 3-nitrobenzoic acid | 200 | 21.5 | 179 |
| | 100 | 18 | 150 |
| | 50 | 16.5 | 138 |
| | 25 | 18 | 150 |
| | 12.5 | 13.5 | 113 |
| | 6.25 | 16 | 133 |
| | 3.12 | 16 | 133 |
| Control | — | 12 | — |
| Positive Control A | 60 | 21.5 | 179 |
| 2,2'-(9,10-Anthracenediyldimethylidene)bis[1-[4,5-dihydro-1-(4-methoxybenzoyl)-1H—imidazol-2-yl]hydrazide] of 4-methoxybenzoic acid | 200 | 16 | 139 |
| Control | — | 11.5 | — |
| Positive Control B | 25 | 16 | 139 |
| 2,2'-[9,10-Anthracenediylbis(methylidyne-1-hydrazinyl-2-ylidene)]bis[4,5-dihydro-1H—imidazole-1-carboxylic acid], bis(1,1-dimethylethyl) ester | 50 | 31.5 | 274 |
| | 25 | 22 | 191 |
| | 12.25 | 17.5 | 152 |
| Control | — | 11.5 | — |
| Positive Control B | 25 | 16 | 139 |
| 2,2'-(Anthracenediyldimethylidyne)bis[1-[1-(2-furanylcarbonyl)-4,5-dihydro-1H—imidazol-2-yl]hydrazide] of 2-furancarboxylic acid | 200 | 12 | 120 |
| Control | — | 10 | — |
| Positive Control A | 60 | 17 | 170 |
| 2,2'-[9,10-Anthracenediylbis(methylidyne-1-hydrazinyl-2-ylidene) bis[4,5-dihydro]-1H—imidazol-1-carboxaldehyde] | 200 | 12 | 120 |
| | 50 | 12 | 120 |
| Control | — | 10 | — |
| Positive Control A | 60 | 17 | 170 |
| 2,2'-[9,10-Anthracenediylbis[methylidyne-1-hydrazinyl-2-ylidene(4,5-dihydro-1H—imidazole-2,1-diyl)carbonyl]], bis-cyclohexanecarboxylic acid | 25 | 18 | 164 |
| | 12.5 | 16 | 145 |
| | 6.25 | 13.5 | 123 |
| Control | — | 11 | — |
| Positive Control B | 25 | 33 | 300 |
| 2,2'-(9,10-Anthracenediyldimethylidyne)bis[1-[1-(3,3-dimethyl-1-oxobutyl)-4,5-dihydro-1H—imidazol-2-yl]hydrazide] of 3,3-dimethyl butanoic acid | 200 | 13 | 118 |
| | 100 | 12 | 109 |
| Control | — | 11 | — |
| Positive Control A | 60 | 20 | 182 |
| 2,2'-(9,10-Anthracenediyldimethylidyne)bis[1-[4,5-dihydro-1- | 200 | 11.5 | 105 |

TABLE I-continued
Lymphocytic Leukemia P388 Test

| Compound | Dose (mg/kg) | Median Survival (Days) | T/C × 100 % |
|---|---|---|---|
| (1-oxobutyl)-1H—imidazol-2-yl]hydrazide] of butanoic acid | | | |
| Control | — | 11 | — |
| Positive Control B | 25 | 32.5 | 295 |
| 2,2'-[9,10-Anthracene-diylbis(methylidyne-1-hydrazinyl-2-ylidene)] bis[1-acetyl-4,5-dihydro-1H—imidazole] | 50 | 11 | 110 |
| | 25 | 10.5 | 105 |
| | 12.5 | 10.5 | 105 |
| | 6.25 | 10.5 | 105 |
| Control | — | 10 | — |
| Positive Control A | 60 | 11.5 | 115 |
| 2,2'-(9,10-Anthracene-diyldimethylidyne)bis [1-(1-acetyl-4,5-dihydro-1H—imidazol-2-yl)hydrazide] of acetic acid | 100 | 11 | 110 |
| | 50 | 10.5 | 105 |
| | 12.5 | 10.5 | 105 |
| Control | — | 101 | — |
| Positive Control A | 60 | 23 | 230 |
| 2,2'-(9,10-Anthracene-diyldimethylidyne)bis[1-[1-(2-fluorobenzoyl)-4,5-dihydro-1H—imidazol-2-yl] hydrazide]of 2-fluorobenzoic acid | 200 | 12 | 109 |
| | 100 | 13 | 118 |
| | 50 | 13 | 118 |
| | 25 | 12 | 109 |
| Control | — | 11 | — |
| Positive Control A | 60 | 20 | 182 |
| 2,2'-[9,10-Anthracene-diylbis[methylidyne(1-formyl-1-hydrazinyl-2-ylidene)]]bis-[4,5-dihydro-1H—imidazole-1-carboxaldehyde] | 200 | 11.5 | 115 |
| | 50 | 11 | 110 |
| | 12.5 | 10.5 | 105 |
| Control | — | 10 | — |
| Positive Control A | 60 | 17 | 170 |
| 2,2'-(9,10-Anthracene-diyldimethylidyne)bis[1-[4,5-dihydro-1-(2-naphthalenylcarbonyl)-1H—imidazol-2-yl]hydrazide] of 2-naphthoic acid | 100 | 12 | 104 |
| Control | — | 11.5 | — |
| Positive Control B | 12.5 | 19 | 165 |
| 2,2'-(9,10-Anthracene-diyldimethylidyne)bis [1-[1-(4-cyanobenzoyl)-4,5-dihydro-1H—imidazol-2-yl]hydrazide] of 4-cyanobenzoic acid | 200 | 14.5 | 132 |
| | 100 | 14.5 | 132 |
| | 50 | 12.5 | 114 |
| | 25 | 12 | 109 |
| Control | — | 11 | — |
| Positive Control A | 60 | 20 | 182 |
| 2,2'-(9,10-Anthracene-diyldimethylidyne)bis[1-[4,5-dihydro-1-(pentafluoro-1H—imidazol-2-yl]hydrazide] of pentafluorobenzoic acid | 200 | 12 | 109 |
| Control | — | 11 | — |
| Positive Control A | 60 | 20 | 182 |

Melanotic Melanoma B16

The animals used were BDF1 mice, all of one sex, weighing a minimum of 17 g, and all within a 3 g weight range. There were normally 12 animals per test group, and 18 animals per control group. A one gram portion of melanotic melanoma B16 tumor was homogenized in 10 ml of Eagle's Minimum Essential Medium, supplemented with 2% fetal calf serum, and a 0.5 ml aliquot of the homogenate was implanted intraperitoneally into each test mouse. The test compounds were administered intraperitoneally on days 1, 5 and 9 (relative to tumor inoculation) at various doses. The animals were weighed and survivors recorded on a regular basis for 60 days. The median survival time and the ratio of survival time for treated (T)/control (C) animals were calculated. The positive control compound was bis(2-imidazolin-2ylhydrazone) of 9,10-anthracenedicarboxaldehyde dihydrochloride (hereinafter called positive control) given as intraperitoneal injection at a dose of 25 mg/kg on days 1, 5 and 9 (relative to tumor inoculation). The results of this test with representative compounds of the present invention appear in Table II.

TABLE II
Melanotic Melanoma B16 Test

| Compound | Dose (mg/kg) | Median Survival (Days) | T/C × 100 % |
|---|---|---|---|
| 2,2'-(9,10-Anthracene-diylbis(methylidyne-1-hydrazinyl-2-ylidene)] bis[4,5-dihydro-gamma-oxo-1H—imidazole-1-butanoic acid] | 12.5 | 55.5 | 252 |
| | 6.25 | >60 | >273 |
| | 3.25 | >60 | >273 |
| Control | — | 22 | — |
| Positive Control B | 25 | 27 | 123 |
| [9,10-Anthracenediylbis-[methylidyne-1-hydrazinyl-2-ylidene(4,5-dihydro-1H—imidazole-2,1-diyl)]]bisphosphonic acid | 25 | 37.5 | 163 |
| | 6.25 | 35.5 | 154 |
| | 1.56 | 29 | 126 |
| Control | — | 23 | — |
| Positive Control B | 25 | 53 | 230 |
| 2,2'-(9,10-Anthracenediyl-dimethylidyne)bis[1-(1-benzoyl-4,5-dihydro-1H—imidazol-2-yl)hydrazide] of benzoic acid | 200 | 50 | 227 |
| | 100 | 57.5 | 261 |
| | 50 | 40 | 182 |
| | 25 | 32 | 145 |
| | 12.5 | 29.5 | 134 |
| Control | — | 22 | — |
| Positive Control B | 25 | 57.5 | 261 |
| | 12.5 | >60 | >273 |
| 2-[[10-[[Acetyl(1-acetyl-4,5-dihydro-1H—imidazol-2-yl)-hydrazono]methyl]-9-anthracenyl]methylene]-1-(4,5-dihydro-1H—imidazol-2-yl)-hydrazide of acetic acid. | 200 | 40 | 182 |
| | 100 | 37 | 168 |
| | 50 | 29.5 | 134 |
| | 25 | 30 | 136 |
| | 12.5 | 28 | 127 |
| Control | — | 22 | — |
| Positive Control B | 25 | 57.5 | 261 |
| | 12.5 | >60 | >273 |
| 2,2'-[9,10-Anthracene-diylbis(methylidyne-1-hydrazinyl-2-ylidene)] bis[4,5-dihydro-1-(1-oxobutyl)-1H—imidazole] | 200 | 27.5 | 125 |
| | 100 | 28.5 | 130 |
| | 50 | 24.5 | 111 |
| | 25 | 26 | 118 |
| Control | — | 22 | — |
| Positive Control B | 25 | 57.5 | 261 |
| | 12.5 | >60 | >273 |

Lymphocytic Leukemia L1210 Test

The animals used were BDF1 mice, all of one sex, weighing a minimum of 17 g and all within a 3 g weight range. There were 6 mice per test group and 18 in control groups. The tumor transplant was by intraperitoneal injection of 0.5 ml of diluted ascites containing $10^5$ viable L1210 leukemia cells per mouse. The test compounds were administered intraperitoneally on days 1, 5 and 9 (relative to tumor inoculation) at various doses. The animals were weighed and survivors recorded on a regular basis for 30 days. The mean survival time and the ratio of survival time for treated (T)/control(C) animals were calculated. The positive control compound was 5-fluorouracil given intraperitoneally at 60 mg/kg. The results of this test appear in Table III.

TABLE III

Lymphocytic Leukemia L1210 Test

| Compound | Dose (mg/kg) | Median Survival (Days) | T/C × 100 % |
|---|---|---|---|
| 2,2'-[9,10-Anthracene- | 12.5 | 13.2 | 155 |
| diylbis(methylidyne-1- | 6.25 | 12.2 | 144 |
| hydrazinyl-2-ylidene)] | 3.12 | 12.3 | 145 |
| bis[4,5-dihydro-gamma- | 1.56 | 12 | 141 |
| oxo-1H—imidazole-1- | 0.78 | 11.2 | 132 |
| butanoic acid] | 0.39 | 11.5 | 135 |
| Control | — | 8.5 | — |
| 5-Fluorouracil A | 60 | 16.8 | 198 |
| [9,10-Anthracenediyl- | 25 | 17 | 200 |
| bis[methylidyne-1-hydra- | 12.5 | 13.3 | 156 |
| zinyl-2-ylidene(4,5- | 6.25 | 13.2 | 155 |
| dihydro-1H—imidazole-2, | 3.12 | 12.2 | 144 |
| 1-diyl)]]bisphosphonic | 1.56 | 11.5 | 135 |
| acid | 0.78 | 10.7 | 126 |
| Control | — | 8.5 | — |
| Positive Control A | 60 | 16.8 | 198 |

The active compounds of this invention may be administered by the intravenous, intramuscular, or subcutaneous routes. The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage, and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammal to be treated, each unit containing a predetermined quantity of active material calculated to produce the desired therapeutic effect in association with the required pharmaceutical carrier. The specifications for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg, with from about 10 to about 500 mg being preferred. Expressed in proportions, the active compound is generally present in from about 0.1 to about 100 mg/ml of carrier. In the case of compositions containing supplementary active ingredients, the dosages are determined by reference to the usual dose and manner of administration of the said ingedients.

The use of prior art anti-tumor agents in rats, such as bisantrene and amsacrine, has been observed to be accompanied by the pathological precipitation of the free base of the agent within the blood vessel due to basification of their acid addition salts, e.g., the hydrochloride salt, by the blood.

It has now been discovered that the di- and the monophosphoramidic acid derivatives of the anti-tumor compound, bisantrene, provided by this invention exhibit excellent efficacy without the attendant precipitation problems seen in the prior art. Both of these derivatives exist as soluble anionic salts at physiological pH, i.e., 7.4; after their injection, no precipitation was detected in a rat tail-vein model.

In the rat, the diphosphoramidic compound was found to be a pro-drug for bisantrene. The diphosphoramidic compound hydrolyzes rapidly to an intermediate form, the monophosphoramidic acid, and this, in turn, slowly hydrolyzes further to bisantrene after distribution of the drug throughout the animal. These in vivo hydrolyses are apparently enzymatic because the diphosphoramidic compound has been shown to be much more stable in water. Furthermore, the stability in water is more than adequate for an efficient formulation via lyophilization. This invention will be described in greater detail in conjunction with the following specific examples.

EXAMPLE 1

Bis(2-imidazolin-2-ylhydrazone) of 9,10-anthracenedicarboxaldehyde

To a solution of 60.0 g of bis(2-imidazolin-2-ylhydrazone) of 9,10-anthracenedicarboxaldehyde dihydrochloride (prepared as described in U.S. Pat. No. 4,258,181) in 1400 ml of water was added a solution of 27.0 g of sodium carbonate in 400 ml of water, with vigorous swirling. The resulting suspension was allowed to stand 5 hours, then the solid was collected in a three-liter, coarse porosity sintered glass funnel and washed with three 1.2 liter portions of very dilute aqueous ammonia, at a concentration of 2.0 ml of concentrated ammonia per liter. The ammonia solution enabled satisfactorily rapid filtration by lowering surface tension and preventing peptization of the solid. The last wash was chloride-free and gave 47.2 g of the desired product as a light orange solid, mp 307°–308° C.

EXAMPLE 2

2,2′-(9,10-Anthracenediylbis(methylidyne-1-hydrazinyl-2-ylidene)bis[4,5-dihydro-1-(1-oxobutyl)-1H-imidazole]

To a stirred suspension of 3.19 g of bis(2-imidazolin-2-ylhydrazone) of 9,10-anthracenedicarboxaldehyde (dried in vacuo at about 110° C. for about 15 hours) in 100 ml of N,N-dimethylformamide (dried over 4A molecular sieves), was added 12.66 g of butyric anhydride. All of the solid was dissolved after stirring for 20 minutes. The solution was filtered through a sintered glass funnel. The filtrate was allowed to stand 26 hours at about 23° C. as a crystalline solid separated. The solid was collected by filtration, washed with N,N-dimethylformamide, then with ether to give 1.72 g of the desired product as orange needles.

EXAMPLE 3

2,2′[9,10-Anthracenediylbis(methylidene-1-hydrazinyl-2-ylidene)]bis[4,5-dihydro-gamma-oxo-1H-imidazole-1-butanoic acid]

A suspension of 3.19 g of bis(2-imidazolin-2-yl-ydrazone) of 9,10-anthracenedicarboxaldehyde (dried in vacuo at 111° C. for 15 hours) and 4.80 g of succinic anhydride in 100 ml of dried N,N-dimethylformamide was stirred for 40 minutes, when the solid had dissolved. The hazy solution was filtered and the filtrate allowed to stand at 23° C. for 24 hours. The filtrate was diluted with 500 ml of water and the resulting slightly warm solution was immediately chilled in an ice bath, producing small granular orange crystals and a finely divided yellow colloid. The colloid was decanted and the granular crystals were washed four times by decantation with cold water, then collected by filtration to give 2.84 g of the desired product as an orange solid, mp 129°–133° C.

EXAMPLE 4

[9,10-Anthracenediylbis[methylidyne-1-hydrazinyl-2-ylidene(4,5-dihydro-1H-imidazole-2,1-diyl)]]bisphosphonic acid, tetraethyl ester To a stirred suspension of 7.969 g of dried bis-(2-imidazolin-2-ylhydrazone) of 9,10-anthracenedicarboxaldehyde in 400 ml of dried dichloromethane under argon was added with stirring via hypodermic syringes and a rubber septum, first 8.137 g of N,O-bis(trimethylsilyl)-acetamide, then 6.902 g of diethyl chlorophosphate. The solid all dissolved after stirring for about 3 hours. The solution was filtered through 200 g of dry-packed, air-equilibrated neutral alumina, (ICN, "for dry-column chromatography") in a 3.8 cm×18 cm column. The colored part of the eluate was collected (cut 1) and the column was eluted with an additional 5×200 ml of dichloromethane to obtain cuts 2–6. Cuts 1–4 were combined and concentrated to 40 ml, then 100 ml of toluene was gradually added to the boiling mixture, with swirling, as a crystalline solid separated and the volume boiled down to 100 ml with bp 100° C. The solid which crystallized was washed with toluene, then with methanol to give 4.36 g of the desired product as orange needles, mp 217° C.

EXAMPLE 5

[9,10-Anthracenediylbis[methylidyne-1-hydrazinyl-2-ylidene(4,5-dihydro-1-H-imidazole-2,1-diyl)]]bisphosphonic acid, tetraphenyl ester To a stirred suspension of 1.99 g of dried bis-(2-imidazolin-2-ylhydrazone) of 9,10-anthracenedicarboxaldehyde in 100 ml of dried dichloromethane were added, under argon as described in Example 4, 2.03 g of N,O-bis(trimethylsilyl)acetamide "BSA" and 2.68 g of diphenyl phosphorochloridate. After one hour of stirring all of the solid had dssolved. Stirring was continued for 2 hours longer. The reaction solution was poured into a 3.8 cm×18 cm dry column of 200 g of air-equilibrated alumina. The column was developed with dichloromethane and the first 100 ml of colorless eluate was discarded, then as the first yellow band neared the bottom, elution cuts of 100 ml each were collected and evaporated. The residue from the first cut, 1.74 g, was dissolved in about 13 ml of dichloromethane, then 40 ml of toluene was added and the solution was heated to boil off the dichloromethane, reduce the volume to about 25 ml and crystallize a solid. The solid was collected by filtration and washed with toluene, then with ether to give 1.65 g of the desired product as an orange solid, mp 214°–215° C.

EXAMPLE 6

[9,10-Anthracenediylbis[methylidyne-1-hydrazinyl-2-ylidene(4,5-dihydro-1H-imidazole-2,1-diyl)]]bisphosphonic acid To a stirred orange solution of 8.74 g of the tetraethyl ester of [9,10-anthracenediylbis-[methylidyne-1-hydrazinyl-2-ylidene(4,5-dihydro-1H-imidazole-2,1-diyl)]]-bis phosphonic acid in 150 ml of dried dichloromethane under argon was added 13.0 g of iodotrimethylsilane via a glass hypodermic syringe and rubber septum. There was a slight exothermic reaction to about 40° C. and the solution became yellow. Within 5 minutes it was orange again. After 30 minutes the solution was evaporated to dryness in vacuo. The glassy residue solidified when suspended in 150 ml of acetone containing 5.2 ml of water to hydrolyze the intermediate silyl ester. The suspension was stirred for 16 hours. The solid was collected and washed with acetone to give 8.17 g of yellow solid. This solid was recrystallized by dissolving it in 200 ml of methanol containing 5.94 ml of triethylamine, thus forming a soluble phosphoramidic acid salt. The free phosphoramidic acid was precipitated by adding 1.82 ml of 97% formic acid. The solid was collected by filtration and washed with ethanol to give 6.04 g of yellow solid which turned orange when dried, mp 235°–238° C.

EXAMPLE 7

2,2'-(9,10-Anthracenediyldimethylidyne)bis[1-(1-benzoyl-4,5-dihydro-1H-imidazol-2-yl)hydrazide]of benzoic acid The procedure of Example 4 was followed while reacting 1.99 g of dried bis(2-imidazolin-2-ylhydrazone) of 9,10-anthracenedicarboxaldehyde, 2.034 g of N,O-bis(trimethylsilyl)acetamide and 1.406 g of benzoyl chloride in 100 ml of dried dichloromethane. The suspension was stirred for 2 days at 24° C. and then was filtered to remove some insoluble orange solid which was washed with dichloromethane. The filtrate and washes were passed through 50 g of air-equilibrated alumina in a 2.3 cm×13.0 cm column. The initial colorless eluate was collected as cut 1. Further elution with dichloromethane gave 50 ml each of cuts 2–5. The eluates were evaporated and the residues from cuts 1 and 2 were washed with ether and combined to give 1.205 g of the desired product as an orange solid, mp 111°–114° C.

EXAMPLE 8

2,2'-[9,10-Anthracenediylbis(methylidyne-1-hydrazinyl-2-ylidene)]bis[4,5-dihydro-delta-oxo-1H-imidazole-1-pentanoic acid]

A mixture of 3.19 g of bis(2-imidazolin-2-ylhydrazone) of 9,10-anthracenedicarboxaldehyde and 5.48 g of glutaric anhydride in 100 ml of dried N,N-dimethylformamide was stirred at 24° C. for 23 hours. The solution was evaporated in vacuo at 35° C. The residue was diluted with 20 ml of dry N,N-dimethyl formamide and swirled to dissolve the residue, then 100 ml of dry ether was added and the mixture was swirled and allowed to stand for several hours. The precipitate which formed was collected and washed with ether to give 4.81 g of the desired product as an orange solid, mp 218°–221° C.

EXAMPLE 9

2,2'-[9,10-Anthracenediylbis(methylidyne-1-hydrazinyl-2-ylidene)]bis[4,5-dihydrol]-1H-imidazole-1-carboxaldehyde To a stirred suspension of 3.98 g of dried bis-(2-imidazolin-2-ylhydrazone) of 9,10-anthracenedicarboxaldehyde in 50 ml of dried N,N-dimethylformamide was added 10.0 ml of phenyl formate. Stirring was continued for 37 hours at 21° C.; the red-orange suspension had gradually changed to yellow in the first hour. Filtration and washing with acetone gave 4.61 g of the desired product as a yellow solid, mp 280°–281° C.

EXAMPLE 10

2,2'-[9,10-Anthracenediylbis(methylidyne-1-hydrazinyl-2-ylidene)]bis[4,5-dihydro]-1H-imidazole-1-carboxylic acid], bis(1,1-dimethylethyl) ester To a solution of 6.55 g of di-tert-butyl dicarbonate in 100 ml of dry N,N-dimethylformamide was added 3.98 g of dried bis(2-imidazolin-2-ylhydrazone) of 9,10-anthracenedicarboxaldehyde. The suspension was protected with a drierite tube (to allow by-product carbon dioxide to escape) and was stirred at 22° C. for 15 hours to give a yellow solution. A 60 ml portion of water was added to the solution until the first sign of turbidity. A clear gum (A) gradually separated. After standing for 2 hours the supernatant was decanted from the gum and filtered through a filter paper cone over about 16 hours. The filtrate gradually deposited orange crystals. After 24 hours the crystals were collected and washed twice with N,N-dimethylformamide/water, 25/10, then twice with water to give 1.29 g of yellow solid (B). The gum (A) crystallized on standing and this material was washed as for (B) above to give 0.59 g of yellow solid (C). The combined clear filtrate and the N,N-dimethylformamide/water wash from (B) above was diluted to 300 ml with water. The resulting emulsion was allowed to stand for 15 hours, then the agglomerated material was collected by filtration and washed with water to give 3.06 g of a yellow solid (D). A solution of combined yellow solids (B) and (C) 1.68 g in 10 ml of dichloromethane was chromatographed on 8.40 g of neutral alumina (ICN, "for dry-column chromatography") in a 1.0 cm×8.0 cm column, eluting with dichloromethane until the yellow band eluted. Evaporation of the eluate gave 1.81 g of a yellow glass. The glass was covered with 30 ml of petroleum ether and mixed, then was allowed to stand for 16 hours. The material recrystalized and was collected by filtration, and washed with ether to give 1.37 g of bis-(1,1-dimethylethyl)-2,2'-[9,10-anthracenediylbis[methylidyne[1-[(1,1-dimethylethoxy)carbony-1-1-hydrazinyl-2-ylidene]]bis[4,5-dihydro-1H-imidazole-1-carboxylate]as a yellow solid, mp 190°–191° C.

A 2.94 g amount of the yellow solid (D) was washed three times with ether leaving 1.84 g of an orange solid. The orange solid (1.84 g) was pulverized and triturated with 50 ml of dichloromethane, then filtered. The orange solid on the filter was washed with dichloromethane. The filtrate and washes were combined and repeatedly refiltered through a pad of diatomaceous earth, then the filtrate was subjected to dry column chromatography on 200 g of air equilibrated silica gel (ICN Co., "for dry-column chromatography") in a 3.4×50.0 cm mylon column, developing the column with 200 ml of chloroform/methanol, 19/1. The fastest yellow band moved only to Rf 0.35 as solvent reached the bottom. The following bands were cut out and extracted on small fritted-glass funnels with chloroform/methanol, 3/1, and the extracts were evaporated to obtain the residues.

| Extract No. | RF of Band on Column (Color) | | Residue Wt. and Color | |
| --- | --- | --- | --- | --- |
| 1 | 0.0–0.05 | (tan) | 0.02 g | Yellow solid |
| 2 | 0.06–0.15 | (light orange) | 0.03 g | Pale orange solid |
| 3 | 0.16–0.25 | (light yellow) | 0.44 g | Orange solid |
| 4 | 0.26–0.35 | (orange tan) | 0.81 g | Orange solid |

The residue of extract 4, 0.81 g, was dissolved in 5.0 ml of dichloromethane, then was filtered and the filtrate evaporated to give a glassy residue. The residue was swirled with about 20 ml of ether and allowed to stand. Then the solid was collected and washed with ether to give 0.50 g of the desired product as a yellow orange solid, mp 148°–151° C.

EXAMPLE 11

2,2'-[9,10-Anthracenediylbis(methylidyne-1-hydrazinyl-2-ylidene)]bis[4,5-dihydro-1-[(4-methylphenyl)sulfonyl]-1H-imidazole]

The procedure of Example 4 was followed while reacting 1.99 g of dried bis(2-imidazolin-2-ylhydrazone) of 9,10-anthracenedicarboxaldehyde, 2.034 g of N,O-bis(trimethylsilyl)acetamide and 1.91 g of p-toluenesulfonyl chloride in 100 ml of dried dichloromethane. The suspension was stirred at 24° C. for 44 hours, then was filtered to remove some insoluble orange solid, and washed with dichloromethane. The filtrate and washes were passed through 50.0 g of air-equilibrated alumina. The initial colorless eluate was discarded and additional dichloromethane was added as seven 50 ml cuts were collected. The first two cuts were evaporated and the residue washed sparingly with chloroform to give 1.10 g of the product of the example, mp 255°–258° C.

EXAMPLE 12

2,2'-[9,10-Anthracenediylbis[methylidyne-1-hydrazinyl-2-ylidene(4,5-dihydro-1H-imidazole-2,1-diyl)carbonyl]]biscyclohexanecarboxylic acid A suspension of 3.19 g of bis(2-imidazolin-2-ylhydrazone) of 9,10-anthracenedicarboxaldehyde and 5.4 g of trans-1,2-cyclohexanedicarboxylic anhydride in 100 ml of dried N,N-dimethylformamide was stirred at 24° C. for 3 hours. The clear solution was concentrated in vacuo to near dryness then was slurried with 100 ml of ether. The solid that formed was collected by filtration, washed with ether and dried in vacuo to give 6.7 g of the desired product.

EXAMPLE 13

2,2'-(9,10-Anthracenediyldimethylidyne)bis[1-[4,5-dihydro-1-(methoxyacetyl)-1H-imidazol-2-yl]hydrazide] of methoxyacetic acid The procedure of Example 4 was followed while reacting 1.99 g of dried bis(2-imidazolin-2-ylhydrazone) of 9,10-anthracenedicarboxaldehyde, 4.069 g of N,O-bis(trimethylsilyl)acetamide and 2.17 g of methoxyacetyl chloride in 100 ml of dried dichloromethane. The reaction mixture was allowed to stir at room temperature for 64 hours, then was filtered to remove some unreacted material and washed with dichloromethane. The filtrate and washes were chromatographed through 50 g of Bio Sil A (Bio-Rad Laboratories). The column was eluted first with 150 ml of dicloromethane for cuts 1 and 2, 250 ml of dichloromethane with 2% methanol for cuts 3 and 4, 100 ml of dichloromethane with 3% methanol for cuts 5 and 6, 100 ml of dichloromethane with 4% methanol for cut 7 and 100 ml of dichloromethane with 5% methanol for cut 8. The cuts were made by using visual observation to separate the three bands on the column. The cuts were evaporated in vacuo. The residue from cut 5 (1.635 g), derived from the largest (middle) band, was recrystallized from dichloromethane/tert-butyl methyl ether to give the desired product as a fine yellow powder, mp 225°–229° C.

EXAMPLES 14–24

Additional acid chloride acylation products of bis(2-imidazolin-2-ylhydrazone) of 9,10-anthracenedicarboxaldehyde listed in Table IV were prepared in the manner described by the procedures of Examples 4, 5 and 13, reacting the given acid chloride with 5 mmol of the above base compound in the presence of an acid binding agent such as N,O-bis(trimethylsilyl)acetamide in a dried solvent such as dichloromethane or N,N-dimethylformamide with stirring for 12–74 hours, then employing column chromatography on alumina (neutral), Bio Sil A or silica gel and elution with a solvent such as dichloromethane, dichloromethane/methanol, acetone and the like to separate the desired product.

TABLE IV

| Ex. | Acid chloride | Product Name | Yield(g) | MP °C. |
|---|---|---|---|---|
| 14 | 4-hexylbenzoyl chloride | 2,2'-(9,10-Anthracenediyldimethylidyne)bis[1-[1-(4-hexylbenzoyl)-4,5-dihydro-1H—imidazol-2-yl]hydrazide] of 4-hexylbenzoic acid | 4.347 | 83–98 |
| 15 | 3-nitrobenzoyl chloride | 2,2'(9,10-Anthracenediyldimethylidyne)bis[1-[4,5-dihydro-1-(3-nitrobenzoyl)-1H—imidazol-2-yl]hydrazide] of 3-nitrobenzoic acid | 1.913 | 162–175 |
| 16 | 2-furoyl chloride | 2,2'-(9,10-Anthracenediyldimethylidyne)bis[1-[1-(2-furanylcarbonyl)-4,5-dihydro-1H—imidazol-2-yl]hydrazide] of 2-furancarboxylic acid | 2.310 | 210–213 |
| 17 | 4-methoxybenzoyl chloride | 2,2'-(9,10-Anthracenediyldimethylidyne)bis[1-[4,5-dihydro-1-(4-methoxybenzoyl)-1H—imidazol-2-yl] hydrazide] of 4-methoxybenzoic acid | 1.332 | 209–211 |
| 18 | 4-cyanobenzoyl chloride | 2,2'-(9,10-Anthracenediyldimethylidyne)bis[1-[1-(4-cyanobenzoyl)-4,5-dihydro-1H—imidazol-2-yl] hydrazide] of 4-cyanobenzoic acid | 0.510 | 178–185 |
| 19 | pentafluorobenzoyl chloride | 2,2'-(9,10-Anthracenediyldimethylidyne)bis[1-[4,5-dihydro-1-(pentafluoro-1H—imidazol-2-yl)hydrazide] of pentafluorobenzoic acid | 1.190 | 145–150 |
| 20 | tert.-butylacetyl chloride | 2,2'-(9,10-Anthracenediyldimethylidyne)bis[1-[1-(3,3-dimethyl-1-oxobutyl)-4,5-dihydro-1H—imidazol-2-yl]-hydrazide] of 3,3-dimethylbutanoic acid | 1.682 | 90–99 |
| 21 | 2-fluorobenzoyl chloride | 2,2'-(9,10-Anthracenediyldimethylidyne)bis[1-[1-(2-fluorobenzoyl)-4,5-dihydro-1H—imidazol-2-yl] hydrazide] of 2-fluorobenzoic acid | 3.383 | 167–175 |
| 22 | 2-naphthyl chloride | 2,2'-(9,10-Anthracenediyldimethylidyne)bis[1-[4,5-dihydro-1-(2-naphthalenylcarbonyl)-1H—imidazol-2-yl]-hydrazide] of 2-naphthoic acid | 2.147 | 175–182 |
| 23 | acetyl chloride | 2,2'-(9,10-Anthracenediyldimethylidyne)bis[1-(1-acetyl-4,5-dihydro-1H—imidazol-2-yl)hydrazide] of acetic acid | 1.184 | 233–235 |

TABLE IV-continued

| Ex. | Acid chloride | Product Name | Yield(g) | MP °C. |
| --- | --- | --- | --- | --- |
| 24 | butyryl chloride | 2,2'-(9,10-Anthracenediyldimethylidyne)bis[1-[4,5-dihydro-1-(1-oxobutyl)-1H—imidazol-2-yl]hydrazide] of butanoic acid | 2.220 | 190–193 |

EXAMPLE 25

2,2'-[9,10-Anthracenediylbis(methylidyne-1-hydrazinyl-2-ylidene)]bis[4,5-dihydro-1H-imidazole-1-sulfonic acid], compound with N,N-diethylethanamine (1:2)

To a mixture of 1.99 g of dried bis(2-imidazolin-2-ylhydrazone) of 9,10-anthracenedicarboxaldehyde and 5.44 g of sulfur trioxide triethylamine complex was added 50 ml of dried N,N-dimethylformamide. The orange suspension was stirred at about 21° C. for 25 hours. The solid was collected by filtration, washed with N,N-dimethylformamide, then ether to give 2.42 g of the desired product as a light orange solid, mp 285°–290° C.

EXAMPLE 26

2,2'-[9,10-Anthracenediylbis(methylidyne-1-hydrazinyl-2-ylidene)]bis[4,5-dihydro-alpha-oxo-1H-imidazole]-propanesulfonic acid]

When a suspension of dried bis(2-imidazolin-2-ylhydrazone) of 9,10-anthracenedicarboxaldehyde and two equivalents of 3-sulfopropionic anhydride [M. S. Kharasch and H. C. Brown, J. Amer. Chem. Soc., 62, 925 (1940)] in 100 ml of dried N,N-dimethylformamide is reacted by the procedure of Example 3, the product of the example is obtained.

EXAMPLE 27

2,2'-[9,10-Anthracenediylbis(methylidyne-1-hydrazinyl-2-ylidene)]bis[4,5-dihydro-N,N,N-trimethyl-3-oxo-1H-imidazole-1-ethanaminium]dichloride To 3.98 g of dried bis(2-imidazolin-2-ylhydrazone) of 9,10-anthracenedicarboxaldehyde and 5.13 g of chloroacetic anhydride was added 100 ml of dried N,N-dimethylformamide. The mixture was swirled for one minute, when all solids had dissolved. After 10 minutes, 45 ml of a solution of 5.0 g of trimethylamine in 100 ml of acetonitrile was added with stirring, causing a slight rise in temperature. After 10 minutes a gummy solid began to separate. After standing for 17 hours the supernatant liquid was decanted and the residual solid was washed by decantation with two 5 ml portions of N,N-dimethylformamide, then was dried in vacuo to give the desired product as an orange solid.

EXAMPLE 28

2,2'-[9,10-Anthracenediylbis(methylidyne-1-hydrazinyl-2-ylidene)]bis[1-acetyl-4,5-dihydro-1H-imidazole To a suspension of 1.992 g of dried bis(2-imidazolin-2-ylhydrazone) of 9,10-anthracenedicarboxaldehyde in 100 ml of dried dichloromethane was gradually added 8.0 ml of acetic anhydride. The solid all rapidly dissolved and then a yellow solid immediately began to separate. After five hours the solid was collected and washed with dichloromethane to give 1.98 g of the desired product as a yellow solid, mp 296°–299° C.

EXAMPLE 29

2-[[10-[[Acetyl(1-acetyl-4,5-dihydro-1H-imidazol-2-yl)hydrazono]methyl]-anthracenyl]methylene]-1-(4,5-dihydro-1H-imidazol-2-yl)hydrazide of acetic acid To a suspension of 1.992 g of dried bis(2-imidazolin-2-ylhydrazone) of 9,10-anthracenedicarboxaldehyde in 100 ml of dried N,N-dimethylformamide was added 5.0 ml of acetic anhydride. In 15 minutes all of the solid had dissolved and yellow crystals began to separate. After 4 hours the solid was collected and washed three times with dry N,N-dimethylformamide. The filtrate and washes were combined and evaporated in vacuo. The residue was re-evaporated three times with 10 ml portions of dry N,N-dimethylformamide, then dried finally at 60° C. in vacuo to remove a trace odor of acetic anhydride. The residue was agitated with 25 ml of dichloromethane and the undissolved solids were removed by filtration. The filtrate was evaporated to give a slightly tacky, glassy residue that hardened while standing under 25 ml of dry ether for 16 hours. The solid was collected and washed with ether to give 0.97 g of the desired product as a yellow solid, melting at 283° C.

EXAMPLE 30

2,2'-[9,10-Anthracenediylbis[methylidyne(1-formyl-1-hydrazinyl-2-ylidene)]]bis[4,5-dihydro-1H-imidazole-1-carboxaldehyde]

A magnetically stirred suspension of 3.98 g of dried bis(2-imidazolin-2-ylhydrazone) of 9,10-anthracenedicarboxaldehyde in 100 ml of dried N,N-dimethylformamide was maintained at 3°–5° C. with an ice bath during the portionwise addition, over a 5 minute period, of 8.29 g of freshly prepared trimethylacetic formic anhydride 15 [E. J. Vlietstra, et al., Res. Trav. Chim., 101, 460 (1982), kept at −80° C. as a solid, then thawed just before use]. Within another 5 minutes all of the solid had dissolved to give a hazy solution. The solution was filtered and the filtrate was allowed to stand at 23° C. for 64 hours. The crystals which had separated were collected and washed with acetone to give 5.11 g of the desired product as yellow-orange crystals, mp 296°–301° C. (dec.).

EXAMPLE 31

[S-(R*,R*)] [9,10-Anthracenediylbis[methylidyne-1-hydrazinyl-2-ylidene(4,5-dihydro-1H-imidazole-2,1-diyl)(1-methyl-2-oxo-2,1-ethanediyl)]]bis carbamic acid, bis(1,1-dimethylethyl)ester A suspension of 3.985 g of dried bis(2-imidazolin-2-ylhydrazone) of 9,10-anthracenedicarboxaldehyde in 200 ml of dried dichloromethane containing 12.068 g of tert-butyl-oxycarbonyl-L-alanine-O-succinimide was sonicated at 18°–23° C. for 3 hours and then filtered, washing with dichloromethane. The filtrate was chromatographed on 100 g of aluminum oxide, eluting with dichloromethane. After the eluate became yellow, the next 225 ml was evaporated. The residue was dissolved in 200 ml of dimethylformamide at 13° C. To this was added 5.48 ml of N-methylmorpholine and then a solution of 2.25 g of glycine in 20 ml of water to destroy excess acylating agent. The resulting solution was stirred at 23° C. for 40 minutes, then chilled in an ice bath and diluted with 600 ml of ice cold water. The solid was collected and washed with water, giving 4.69 g of the desired product, mp 148°–155° C.

EXAMPLE 32

[S-(R*,R*)][9,10-Anthracenediylbis(methylidyne-1-hydrazinyl-2-ylidene)]bis[1-(2-amino-1-oxopropyl)-4,5-dihydro-1H-imidazole]tetrahydrochloride A solution of 4.13 g of [S-(R*,R*)[9,10-anthracenediylbis[methylidyne-1-hydrazinyl-2-ylidene-(4,5-dihydro-1H-imidazole-2,1-diyl) (1-methyl-2-oxo-2,1-ethanenediyl)]]bis carbamic acid, bis(1,1-dimethylethyl)ester in 40 ml of glacial acetic acid and 20 ml of anisole was cooled in a water bath at 16° C. as hydrogen chloride was bubbled in for 3 minutes. After standing for 30 minutes the solid was collected, washed with two 35 ml portions of glacial acetic acid and four times with acetone, giving 3.61 g of the desired product, mp 205°–208° C.

EXAMPLE 33

2,2'[9,10-Anthracenediylbis(methylidene-1-methyl-1-hydrazinyl-2-ylidene)]bis[4,5-dihydro-gamma-oxo-1H imidazole]-1-butanoic acid A suspension of 16.2 g of bis(2-imidazolin-2-ylmethylhydrazone) of 9,10-anthracenedicarboxaldehyde dihydroiodide in water was stirred with 12.0 g of sodium carbonate at 50°–70° C. for one hour, then cooled. The solid was washed with water and dried to give 9.8 g of the free base. Subsequent acylation with succinic anhydride by the procedure of Example 3 gives the title compound as an orange solid.

EXAMPLE 34

[9,10-Anthracenediylbis[methylidyne-1-hydrazinyl-2-ylidene (4,5-dihydro-1H-imidazol-2,1-diyl)]]phosphonic acid, diethyl ester To a 3 liter round bottom flask equipped with a stirring bar was added, under argon, 41.456 g of the bis(2-imidazolin-2-ylhydrazone) of 9,10-anthracenedicarboxaldehyde, (not specially dried and therefore hydrated), 2 liters of dichloromethane, 42.33 g (51.43 ml) of N,O-bis(trimethylsilyl) acetamide via a syringe and 35.90 g (30.07 ml) of diethyl chlorophosphate also via a syringe. After stirring overnight, the cloudy orange mixture was filtered. The filtrate was chromatographed on 1 kg of partially deactivated (air equilibrated) alumina and developed with dichloromethane. Nine 1 liter fractions were taken and partially concentrated. Fractions 1–3 gave the product of Example 4. Fractions 4–7 were combined and further concentrated, giving 13.31 g of solid.

A 13.01 g portion of the above solid in a fritted funnel was washed sparingly with 30, 20 and 10 ml of dichloromethane and then with water, giving 6.50 g of orange solid. This solid was mixed with 200 ml of hot dichloromethane and filtered through 3 g of silica gel, washing with 40 ml of dichloromethane. The filtrate was concentrated to about 30 ml. The resulting solid was collected and washed with a minimum of cold dichloromethane and then with carbon tetrachloride, giving 4.50 g of the desired product as yellow leaflets, mp 195°–202° C. Thin layer chromatography on silica gel vs. chloroform/methanol (9/1), gave a spot with Rf 0.3 as compared with Rf 0.6 for the product of Example 4.

EXAMPLE 35

[9,10-Anthracenediylbis[methylidyne-1-hydrazinyl-2-ylidene (4,5-dihydro-1H-imidazol-2,1-diyl)]] phosphonic acid hydroiodide To a solution of 1.07 g of dried [9,10-anthracenediylbis[methylidyne-1-hydrazinyl-2-ylidene (4,5dihydro-1H-imidazole-2,1-diyl)]]phosphonic acid, diethyl ester and 5.25 g of triphenylphosphine in 90 ml of dried dichloromethane, under argon, was added, via a syringe, 1.0 g (0.71 ml) of iodotrimethylsilane. After 30 minutes, the clear orange solution was evaporated to dryness and then re-evaporated twice from 50 ml portions of dry dichloromethane. The residue was suspended in 50 ml of acetone and 1 ml of water was added, precipitating an orange gum. The gum was pressed thin and allowed to stand overnight in the moist acetone under argon. The gum solidified. It was then pulverized, collected and washed with acetone, giving 1.21 g of the desired product as an orange solid; MS ((+)FAB)479(M+H); NMR (300 MHz, Me$_2$SO-d$_6$:)$\delta$1.23 (t,3,C—CH$_3$), 3.77 (s, NCH$_2$CH$_2$N), 3.85 (m, CH$_2$ of Et), 7.70 (h,4,arom.), 8.44 and 8.49 (m,4,arom.), 8.78 (s,1,NH), 9.04 (s,1,NH), 9.34 (s,1,CH=N), 9.43 (s,1,CH=N), 12.54 (s,1,C=N'H+).

EXAMPLE 36

[2-[[[10-[[(4,5-Dihydro-1H-imidazol-2-yl) ethylhydrazono]methyl]-9-anthracenyl]methylene]hydrazino]-4,5-dihydro-1H-imidazol-1-yl]phosphonic acid, hydroiodide The procedure of Example 35 was followed except that no triphenylphosphine was used to remove by-product ethyl iodide. A solution of the crude, solidified reaction product in 10 ml of methanol was filtered through 1 g of alumina in a 0.6 cm column, washing with 5 ml of methanol. The filtrate was evaporated almost to dryness when the residual syrup began to crystallize. A 20 ml portion of acetone was added, the solid was macerated and then allowed to stand overnight. The solid was collected and washed with acetone, giving 1.057 g of the desired product; MS ((+)FAB)479(M+H); NMR (300 MHz, Me$_2$SO-d$_6$)$\delta$3.77 (s,8,NCH$_2$CH$_2$N), 7.66 (m,4,arom.), 8.49 (h,4,arom.), 8.79 (s,2,NH), 8.92 (s,1,NH), 9.34 and 9.36 (d,2,CH=N), 12.58 (d,1,C=N'H+).

EXAMPLE 37

Disodium [9,10-anthracenediylbis [methylidyne-1-hydrazinyl-2-ylidene (4,5-dihydro-1H-imidazole-2,1-diyl)]] bis [phosphate]

To a stirred suspension of 585 mg of the compound prepared according to Example 6, [9,10-anthracenediylbis[methylidyne-1-hydrazinyl-2-ylidene (4,5-dihydro-1H-imidazole-2,1-diyl)]]bisphosphonic acid in 10 ml of water, monitored by a pH meter, was added dropwise 18.3 ml of 0.1N sodium hydroxide, at a rate such that the pH never exceeded 7.5 and gave a final pH of 7.4. This solution was evaporated at 35° C. over 5 hours, giving 629 mg of the desired product as an amorphous red-orange solid.

The compound prepared according to Example 37 was tested in the rat tail vein model for phlebitis reaction near the site of injection. For comparison purposes, a control placebo and bisantrene were also tested. The compounds were administered intravenously in an amount of 25 mg/kg. Observations were made at 1, 5 and 9 days following the injection.

No evidence of phlebitis was seen in the rat tail vein model that was administered the compound prepared according to Example 37, in contrast to bisantrene which did produce evidence of phlebitis near the site of injection.

What is claimed is:

1. A compound selected from those of the formula:

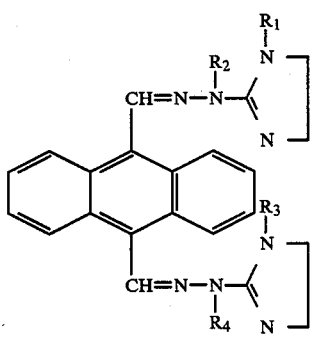

wherein $R_1$ and $R_3$ are the same or different and are: hydrogen, alkyl($C_1$–$C_6$),

((where $R_5$ is hydrogen, alkyl($C_1$–$C_6$), cyclohexyl which is further substituted by carboxyl, phenyl, monosubstituted phenyl (wherein the substituent may be ortho, meta or para and is fluoro, nitro, alkyl($C_1$–$C_6$), alkoxy ($C_1$–$C_3$) or cyano), pentafluorophenyl, naphthyl, furanyl, —CHNHCOOC($CH_3$)$_3$, —CHNH$_2$,
 |                                 |
 CH$_3$                            CH$_3$

—CH$_2$CH$_2$COOH,  —OC(CH$_3$)$_3$,  —CH$_2$OCH$_3$,
—(CH$_2$)$_3$COOH,

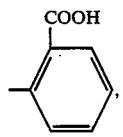

—(CH$_2$)$_2$SO$_3$H or —CH$_2$N$^{\oplus}$—(CH$_3$)$_3$Cl$^{\ominus}$)),

—P(OH)$_2$, —P(OC$_2$H$_5$)$_2$, —P(O—⌬)$_2$,
  ∥         ∥                 ∥
  O         O                 O

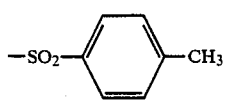

or —SO$_3$H; with the proviso that only one of $R_1$ and $R_3$ may be hydrogen or alkyl($C_1$–$C_6$); $R_2$ and $R_4$ are the same or different and are: hydrogen, alkyl($C_1$–$C_4$) or

((where $R_6$ is hydrogen, alkyl($C_1$–$C_6$), phenyl, monosubstituted phenyl (wherein the substituent may be in the ortho, meta or para position and is fluoro, nitro, alkyl($C_1$–$C_6$), alkoxy ($C_1$–$C_3$)) or cyano), pentafluorophenyl, naphthyl, furanyl or —CH$_2$OCH$_3$)); or a pharmacologically acceptable salt thereof.

2. The compound according to claim 1, 2,2'-[9,10-anthracenediylbis(methylidyne-1-hydrazinyl-2-ylidene)]bis[4,5-dihydro-1-(oxobutyl)-1H-imidazole].

3. The compound according to claim 1, 2,2'-[9,10-anthracenediylbis(methylidyne-1-hydrazinyl-2-ylidene)]bis[4,5-dihydro-1-gamma-oxo-1H-imidazole-1-butanoic acid].

4. The compound according to claim 1, [9,10-anthracenediylbis[methylidyne-1-hydrazinyl-2-ylidene(4,5-dihydro-1H-imidazole-2,1-diyl)]]bisphosphonic acid, tetraethyl ester.

5. The compound according to claim 1, [9,10-anthracenediylbis[methylidyne-1-hydrazinyl-2-ylidene(4,5-dihydro-1H-imidazole-2,1-diyl)]]bisphosphonic acid, tetraphenyl ester.

6. The compound according to claim 1, [9,10-anthracenediylbis[methylidyne-1-hydrazinyl-2-ylidene(4,5-dihydro-1H-imidazole-2,1-diyl]]bisphosphonic acid.

7. The compound according to claim 1, 2,2'-(9,10-anthracenediyldimethylidyne)bis[1-(1-benzoyl-4,5-dihydro-1H-imidazol-2-yl)hydrazide] of benzoic acid.

8. The compound according to claim 1, 2,2'-[9,10-anthracenediylbis(methylidyne-1-hydrazinyl-2-ylidene)]bis[4,5-dihydro-delta-oxo-1H-imidazole-1-pentanoic acid].

9. The compound according to claim 1, 2,2'-[9,10-anthracenediylbis(methylidyne-1-hydrazinyl-2-ylidene)] bis[4,5-dihydro]-1H-imidazole-1-carboxaldehyde.

10. The compound according to claim 1, 2,2'-[9,10-anthracenediylbis(methylidyne-1-hydrazinyl-2-ylidene)]bis(4,5-dihydro-1H-imidazole-1-carboxylic acid], bis(1,1-dimethylethyl)ester.

11. The compound according to claim 1, 2,2'-[9,10-anthracenediylbis(methylidyne-1-hydrazinyl-2-ylidene)]bis[4,5-dihydro-1-(4-methylphenyl)sulfonyl]-1H-imidazole].

12. The compound according to claim 1, 2,2'-[9,10-anthracenediylbis[methylidyne-1-hydrazinyl-2-ylidene(4,5-dihydro-1H-imidazole-2,1-diyl)carbonyl]-]biscyclohexanecarboxylic acid.

13. The compound according to claim 1, 2,2'-(9,10-anthracenediyldimethylidyne)bis[1-[4,5-dihydro-1-(methoxyacetyl)-1H-imidazol-2-yl]hydrazide] of methoxyacetic acid.

14. The compound according to claim 1, 2,2'-(9,10-anthracenediyldimethylidyne)bis[1-[1-(4-hexylbenzoyl)-4,5-dihydro-1H-imidazol-2-yl]hydrazide] of 4-hexylbenzoic acid.

15. The compound according to claim 1, 2,2'-(9,10-anthracenediyldimethylidyne)bis[1-[4,5-dihydro-1-(3-nitrobenzoyl)-1H-imidazol-2-yl]hydrazide] of 3-nitrobenzoic acid.

16. The compound according to claim 1, 2,2'-(9,10-anhracenediyldimethylidyne)bis[1-[1-(2-furanylcarbonyl)-4,5-dihydro-1H-imidazol-2-yl]hydrazide] of 2-furancarboxylic acid.

17. The compound according to claim 1, 2,2-(9,10-anthracenediyldimethylidyne)bis[1-[4,5-dihydro-1-(4-methoxybenzoyl)-1H-imidazol-2-yl]hydrazide] of 4-methoxybenzoic acid.

18. The compound according to claim 1, 2,2'-(9,10-anthracenediyldimethylidyne)bis[1-[1-(4-cyanobenzoyl)-[4,5-dihydro-1H-imidazol-2-yl]hydrazide] of 4-cyanobenzoic acid.

19. The compound according to claim 1, 2,2'-(9,10-anthracenediyldimethylidyne)bis[1-[4,5-dihydro-1-(pentafluoro)-1H-imidazol-2-yl]hydrazide] of pentafluorobenzoic acid.

20. The compound according to claim 1, 2,2'-(9,10-anthracenediyldimethylidyne)bis[1-[1-(3,3-dimethyl-1-oxobutyl)-4,5-dihydro-1H-imidazol-2-yl]hydrazide] of 3,3-dimethylbutanoic acid.

21. The compound according to claim 1, 2,2'-(9,10-anthracenediyldimethylidyne)bis[1-[1-(2-fluorobenzoyl)-4,5-dihydro-1H-imidazol-2-yl]hydrazide] of 2-fluorobenzoic acid.

22. The compound according to claim 1, 2,2'-(9,10-anthracenediyldimethylidyne)bis[1-[4,5-dihydro-1(2-naphthalenylcarbonyl)-1H-imidazol-2-yl]hydrazide] of 2-naphthoic acid.

23. The compound according to claim 1, 2,2'-(9,10-anthracenediyldimethylidyne)bis[1-(1-acetyl-4,5-dihydro-1H-imidazol-2-yl)hydrazide] of acetic acid.

24. The compound according to claim 1, 2,2'-(9,10-anthracenediyldimethylidyne)bis[1-[4,5-dihydro-1-(1-oxobutyl)-1H-imidazol-2-yl]hydrazide] of butanoic acid.

25. The compound according to claim 1, 2,2'-[9,10-anthracenediylbis(methylidyne-1-hydrazinyl-2-ylidene)]bis[4,5-dihydro-1H-imidazole-1-sulfonic acid], compound as the pharmacologically acceptable salt of N,N-diethylethanamine (1:2).

26. The compound according to claim 1, 2,2'-[9,10-anthracenediylbis(methylidyne-1-hydrazinyl-2-ylidene)]bis]4,5-dihydro-alpha-oxo-1H-imidazolepropanesulfonic acid].

27. The compound according to claim 1, 2,2'-(9,10-anthracenediylbis(methylidyne-1-hydrazinyl-2-ylidene)]bis[4,5-dihydro-N,N,N-trimethyl-3-oxo-1H-imidazole-1-ethanaminium]dichloride.

28. The compound according to claim 1, 2,2'-(9,10-anthracenediylbis(methylidyne-1-hydrazinyl-2-ylidene)bis[1-acetyl-4,5-dihydro-1H-imidazole].

29. The compound according to claim 1, 2-[[10[[acetyl(1-acetyl-4,5-dihydro-1H-imidazol-2-yl) hydrazono]-methyl]-9-anthracenyl]methylene]-1-(4,5-dihydro-1H-imidazol-2-yl)hydrazide of acetic acid.

30. The compound according to claim 1, 2,2'-[9,10-anthracenediylbis[methylidyne(1-formyl-1-hydrazinyl-2-ylidene)]]bis[4,5-dihydro-1H-imidazole-1-carboxaldehyde].

31. The compound according to claim 1, [S-(R*,R*)] [9,10-anthracenediylbis[methylidyne-1-hydrazinyl-2-ylidene(4,5-dihydro-1H-imidazole-2,1-diyl)(1-methyl-2-oxo-2,1-ethanediyl)]]biscarbamic acid, bis(1,1-dimethylethyl)ester.

32. The compound according to claim 1, [S-(R*,R*)] [9,10-anthracenediylbis(methylidyne-1-hydrazinyl-2-ylidene)]bis[1-(2-amino-1-oxopropyl)-4,5-dihydro-1H-imidazole]tetrahydrochloride.

33. The compound according to claim 1, 2,2'-[anthracenediylbis(methylidene-1-methyl-1-hydrazinyl-2-ylidene)]bis[4,5-dihydro-gamma-oxo-1H-imidazole]-1-butanoic acid.

34. The compound according to claim 1, [9,10-anthracenediylbis[methylidyne-1-hydrazinyl-2-ylidene (4,5-dihydro-1H-imidazole-2,1-diyl)]]phosphonic acid, diethyl ester.

35. The compound according to claim 1, [9,10-anthracenediylbis(methylidyne-1-hydrazinyl-2-ylidene (4,5-dihydro-1H-imidazole-2,1-diyl)]]phosphonic acid.

36. The compound according to claim 1, [9,10-anthracenediylbis[methylidyne-1-hydrazinyl-2-ylidene (4,5-dihydro-1H-imidazol-2,1-diyl)]]phosphonic acid hydroiodide.

37. The compound according to claim 1, [2-[[[10-[[(4,5-dihydro-1H-imidazol-2-yl)ethylhydrazono]methyl]-9-anthracenyl]methylene]hydrazino]-4,5-dihydro-1H-imidazol-1-yl]phosphonic acid.

38. The compound according to claim 1, [2-[[[10-[[(4,5-dihydro-1H-imidazol-2-yl)ethylhydrozono]methyl]-9-anthracenyl]methylene]hydrazino]-4,5-dihydro-1H-imidazol-1-yl]phosphonic acid, hydroiodide.

39. The compound according to claim 1, disodium 9,10-anthracenediylbis[methylidyne-1-hydrazinyl-2-ylidene(4,5-dihydro-1H-imidazol-2,1-diyl)]] bis[phosphate].

* * * * *